US009254351B2

(12) United States Patent
Barbas

(10) Patent No.: US 9,254,351 B2
(45) Date of Patent: Feb. 9, 2016

(54) METHOD FOR THE SURFACE TREATMENT OF TITANIUM BONE IMPLANTS USING, IN ORDER, A SODIUM HYDROXIDE BATH AND ANODIZATION

(71) Applicant: OBL (Société Anonyme), Châtillon (FR)

(72) Inventor: Alexandre Barbas, Vendôme (FR)

(73) Assignee: OBL (Société Anonyme), Châtillon (FR)

( * ) Notice: Subject to any disclaimer, the term of this patent is extended or adjusted under 35 U.S.C. 154(b) by 2 days.

(21) Appl. No.: 14/358,033

(22) PCT Filed: Nov. 14, 2012

(86) PCT No.: PCT/FR2012/000457
§ 371 (c)(1),
(2) Date: Aug. 12, 2014

(87) PCT Pub. No.: WO2013/072576
PCT Pub. Date: May 23, 2013

(65) Prior Publication Data
US 2014/0377449 A1  Dec. 25, 2014

(30) Foreign Application Priority Data

Nov. 14, 2011 (FR) .................................... 11 03460

(51) Int. Cl.
  A61L 31/16   (2006.01)
  A61L 27/50   (2006.01)
  C25D 11/26   (2006.01)
  A61L 27/06   (2006.01)
  A61L 27/32   (2006.01)

(52) U.S. Cl.
CPC ................ *A61L 31/16* (2013.01); *A61L 27/06* (2013.01); *A61L 27/32* (2013.01); *A61L 27/50* (2013.01);

(Continued)

(58) Field of Classification Search
CPC ................................ A61L 27/06; A61L 27/32
USPC ......................................... 427/2.24, 2.26, 2.27
See application file for complete search history.

(56) References Cited

U.S. PATENT DOCUMENTS 7,767,250 B2 * 8/2010 Luan et al. ..................... 427/2.1

FOREIGN PATENT DOCUMENTS

WO   2009044203 A1   4/2009
WO   WO 2009044203 A1 *   4/2009

OTHER PUBLICATIONS

Feng et al. Controlled crystal growth of calcium phosphate on titanium surface by NaOH-treatment.Journal of Crystal Growth. Apr. 1999; 200(3-4):550-557.*

(Continued)

*Primary Examiner* — Cachet Sellman
(74) *Attorney, Agent, or Firm* — EIP US LLP

(57) ABSTRACT

The invention relates to a method for the surface treatment of a biologically inert titanium implant to be placed in contact with a bone of the human body, which involves allowing body fluids, such as the inorganic portion of human blood plasma, to naturally deposit, onto the titanium implant, a calcium phosphate film having the formula $Ca^5(PO_4)^3(OH)$, in the form of hydroxyapatite, with a view to rendering the biologically inert titanium biologically active so as to enable the bone to chemically bond to the implant, thus promoting osseointegration, the method including an operation that involves submerging the titanium in a sodium hydroxide (NaOH) solution, wherein said submersion causes the formation of a film of hydrated titanium oxides ($HTiO_3$—) on the titanium, which in turn causes hydroxyl groups (TiOH) to appear, thus enabling the deposition of said calcium phosphate film. The method according to the invention is characterized in that it includes, after the operation of submerging the implant in sodium hydroxide, an operation of anodizing the implant at a given voltage, thereby enabling the stabilization of the oxide film formed by means the operation of submerging the implant in the sodium hydroxide.

11 Claims, 4 Drawing Sheets

(52) U.S. Cl.
CPC ............. *C25D 11/26* (2013.01); *A61L 2400/18* (2013.01); *A61L 2420/02* (2013.01); *A61L 2430/02* (2013.01)

(56) References Cited

OTHER PUBLICATIONS

International Search Report issued Apr. 23, 2013 on related application PCT/FR2012/000457 filed Nov. 14, 2012.

Kar, A et al., "Electrodeposition of Hydroxyapatite Onto Nanotubular TiO2 for Implant Applications," Surface and Coatings Technology. vol. 201, No. 6, Dec. 2006 (Dec. 4, 2006), pp. 3723-3731.

Kukobu, T., "Formation of Biologically Active Bone-Like Apatite on Metals and Polymers by a Biomimetic Process," Thermochimica Acta. vol. 280/281, (1996), pp. 479-490.

Liu, Xuanyoug et al., "Surface Nano-Functionalization of Biomaterials," Materials Science and Engineering R. vol. 70, No. 3-6, 22, Nov. 2010 (Nov. 22, 2010), pp. 275-302.

\* cited by examiner

METHOD FOR THE SURFACE TREATMENT OF TITANIUM BONE IMPLANTS USING, IN ORDER, A SODIUM HYDROXIDE BATH AND ANODIZATION

TECHNICAL FIELD OF THE INVENTION

The present invention relates to a method for processing the surface of an implant of bioinert titanium which is intended to be placed in contact with a bone of the human body, the method being intended to render the bioinert titanium bioactive in order to allow a chemical bond of the bone to the implant.

Such a processing operation will therefore promote the osteointegration of the implant processed in this manner at the surface, the connection between the implant and the bone, following this processing operation, being of better quality and obtained more rapidly than with an implant of conventional titanium. It is consequently reasonably possible to anticipate a significant increase of the clinical life-span of the implant solution.

TECHNOLOGICAL BACKGROUND OF THE INVENTION

Documentation has taught us that the materials used for the purposes of implantation in the human body may be of different types.

There are biotolerant materials, bioinert materials and bioactive materials of which some examples appear in Table 1 established by Kienapfel H., Sprey C., Wilke A., Griss P., Implant fixation by bone ingrowth, The Journal of Arthroplasty, Volume 14 No. 3, 1999, which Table 1 also sets out the level of biocompatibility of some of the materials examined in contact with the bone. The distinction between these types of materials is the manner in which they will be accepted by the organism. In this manner, the biotolerant materials will be encapsulated by a fibrous material. Bioinert materials will not bring about a reaction of the living tissues. The bone will be able to grow on these materials without a chemical bond. Conversely, the bioactive materials will integrate excellently in the living environment by creating chemical bonds therewith.

TABLE 1

| Materials | Extent of the biocompatibility | Osteogenesis |
|---|---|---|
| PMMA (Polymethyl methacrylate) | Biotolerant | Remote osteogenesis |
| Stainless steel | Biotolerant | Remote osteogenesis |
| Alumina | Bioinert | Contact osteogenesis |
| Carbon | Bioinert | Contact osteogenesis |
| Titanium and titanium-based alloys | Bioinert | Contact osteogenesis |
| Chromium/cobalt alloys | Bioinert | Osteogenesis with bond |
| Phosphocalcic ceramics | Bioactive | Osteogenesis with bond |

Kokubo T. (see "Bioactive glass ceramics: properties and applications, Biomaterials 12, pages 155-163, 1991" and see also "Formation of biologically active bone-like apatite on metals and polymers by a biomimetic process, Thermochimica Acta 280/281, pages 479-490, 1996") has carried out research concluding that the connection between the titanium and the bone is carried out by means of a film of apatite, in particular in the form of hydroxyapatite which is a mineral species of the phosphate family, having the formula $Ca^5(PO4)^3(OH)$. It is known that titanium is bioinert. The bone can therefore not bond chemically thereto. However, it has been found that, following an implant of titanium, the biological fluids deposit on the implant a film of calcium phosphate which will chemically bond to the titanium of the implant, and it is to this deposit, in which the levels of calcium and phosphorus are in the ratio Ca/P of approximately from 1.57 to 1.62 and whose constitution is therefore very close to that of the human bone, that the bone can chemically bond.

FIG. 1 further shows the method for attaching the bone to an implant in vivo.

To this end, scientists have developed techniques for evaluation of the bioactivity using for this purpose solutions which simulate the mineral portion of human blood plasma and which therefore contain the same ions as the blood plasma, and at equivalent concentrations. Several solutions of this type, referred to as "Simulated Body Fluid" or SBF, have been disclosed over recent years. After the first SBF created by Kokubo in 1991, improvements were made to this fluid so that it represents the mineral portion of the human blood plasma to the greatest possible extent. The chemical properties of the SBF thus allow the bioactivity of a material to be evaluated by immersing it in the SBF fluid for a length of time and observing the surface thereof after drying.

Table 2, communicated by Kokubo T., Takadama H. (How useful is SBF in predicting in vivo bone bioactivity, Biomaterials 27, pages 2907-2915, 2006), further establishes the comparison between the composition of human blood plasma and different SBFs.

TABLE 2

| | Ionic concentration (mM) | | | | | | | |
|---|---|---|---|---|---|---|---|---|
| | $Na^+$ | $K^+$ | $Mg^{2+}$ | $Ca^{2+}$ | $Cl^-$ | $HCO_3^-$ | $HPO_4^{2-}$ | $SO_4^{2-}$ |
| Human blood plasma | 142.0 | 5.0 | 1.5 | 2.5 | 103.0 | 27.0 | 1.0 | 0.5 |
| Starting SBF | 142.0 | 5.0 | 1.5 | 2.5 | 148.8 | 4.2 | 1.0 | 0 |
| Corrected SBF (c-SBF) | 142.0 | 5.0 | 1.5 | 2.5 | 147.8 | 4.2 | 1.0 | 0.5 |
| Revised SBF (r-SBF) | 142.0 | 5.0 | 1.5 | 2.5 | 103.0 | 27.0 | 1.0 | 0.5 |
| Resulting improved SBF | 142.0 | 5.0 | 1.5 | 2.5 | 103.0 | 4.2 | 1.0 | 0.5 |

According to Kokubo, the layer which is indispensable for the connection between the bone and the titanium in vivo can be reproduced in vitro by immersion in the SBF. The capacity of a material to create bonds with the bone corresponds to the capacity thereof to be covered with a layer of apatite when it is immersed in this bodily fluid simulated in vitro. Conversely, the bone colonisation will not be able to be carried out on a material which does not have a deposit of apatite after it has been immersed in the SBF.

The observation of the deposit of apatite can be carried out by means of electronic microscopy and the analysis of the composition of this deposit can be carried out using any chemical analysis method.

Still according to Kokubo, it is consequently possible to compare the bioactivity of several materials by comparing the deposition speed of the apatite on these different materials when they are immersed in SBF.

In 2008, concentrating more specifically on pure titanium, the team of Waléria Silva de Meideros, de Oliveira M. V., Pereira L. C. and Andrade M. C. (Bioactive Porous Titanium: an alternative to surgical implants, Artificial Organs 32(4), pages 277-282, 2008) immersed in SBF porous samples of pure titanium. This team has concluded that, after seven days, a deposit of calcium could be identified. Then, after fourteen days, it was possible for them to observe by means of EDX analysis the presence of calcium and phosphorus. Furthermore, as shown in FIG. 2, it can be seen that after fourteen and twenty-eight days of immersion, respectively, a film of calcium phosphate is present at the surface of the material.

According to Kokubo, in his article mentioned above which appeared in 1996 in "Thermochimica Acta", the layer of apatite which is deposited on the material implanted in the human body is carried out using hydroxyl groups (OH) present on the surface of the material. These hydroxyl groups appear as a result of the action of the biological fluids on the material. A layer containing hydrated titanium oxides ($HTiO_3$—) may be reproduced, for titanium, by immersing it in a solution which contains sodium hydroxide NaOH concentrated at 10 moles per liter. This is because the immersion of the titanium in this solution allows the passive layer of oxide to be dissolved at the surface and a new layer of oxides to be created which are necessary for the attachment of the layer of apatite. The same author informs us that this new layer of oxides is unstable both mechanically and chemically. In order to stabilise it, he carries out a thermal processing operation at 600° C. in order to render this deposit amorphous and crystalline. The presence of this layer facilitates the appearance, at the surface of the material, of hydroxyl groups (TiOH) which will bring about the formation of apatite.

Lenka Jonasova and his team (Jonasova L., üller F. A., Helebrant A., Strnad J., Greil P., Biomimetic apatite formation on chemically treated titanium, Biomaterials 25, pages 1187-1194, 2004) have worked on this same subject-matter. However, for their part, they have sought to improve such a method for processing titanium with sodium hydroxide by preparing the titanium beforehand and, more specifically, by pickling it with a solution containing HCl. According to their work, this prior preparation allows, before the processing with NaOH, a layer of TiO2 to be obtained which is finer and more uniform than without such a pickling operation. Samples which had been processed using this method (HCl, then NaOH) were then immersed in SBF. Following each step, chemical analyses were carried out and suppositions relating to the chemical reactions which had taken place, leading to modifications of the surface of the samples of titanium, were transmitted as can be seen in FIG. 7.

It appears that the pickling is successful in degrading the layer of TiO2 naturally present on the surface of the titanium and that, following this degradation, a layer of TiH2 is formed. In contact with ambient air, a new layer of TiO2 which is finer is formed. The immersion in sodium hydroxide NaOH allows this surface layer of TiO2 to be dissolved and a new titanium oxide which contains $Na^+$ ions to be formed. During the immersion in the SBF, an exchange of ions is produced between this and the surface of the titanium. This leads to the formation of a layer of TiOH. The $Ca^{2+}$ ions are then incorporated into this layer and it is these $Ca^{2+}$ ions which, owing to their positive charge, will allow apatite to be formed on the surface. This is because the ions $(PO_4)^{3-}$ and $(CO3)^{2-}$ will be able to become attached thereto and thus form apatite. The apatite formed in this instance at the surface is HydroxyCarbonated Apatite (HCA), that is to say, a hydroxyapatite which is similar to that naturally present in a bone tissue.

This being the case, no conclusion has been drawn from all these hypotheses formulated in documentation although titanium implants are being increasingly used and porous titanium implants whose characteristics of porosity are very similar to those of the human bone have even recently appeared.

In the wording of a patent application filed in parallel with this one by the same filing company, there has been proposed a new method for processing the surface of a titanium implant by means of immersion in a bath of sodium hydroxide which modifies the layer of oxides naturally present on the titanium and which renders bioactive this metal which is naturally bioinert, which thus allows a strong chemical connection of the bone to the implant produced from such a metal and which consequently promotes the osteointegration of the implant.

The chemical and mechanical stability of the effects of this processing with sodium hydroxide is, however, uncertain.

An object of the present invention is therefore to overcome this possible disadvantage.

GENERAL DESCRIPTION OF THE INVENTION

The present invention therefore first relates to a method for processing the surface of an implant of bioinert titanium which is intended to be placed in contact with a bone of the human body, of the type involving allowing biological fluids, such as the mineral portion of human blood plasma, to deposit naturally on the implant of titanium a film of calcium phosphate, having the formula $Ca^5(PO_4)^3(OH)$, in the form of hydroxyapatite, so as to render the bioinert titanium bioactive in order to allow a chemical bond of the bone to the implant, thus promoting the osteointegration, the method comprising an operation which involves immersing the titanium in a solution which contains sodium hydroxide NaOH whose concentration is in the order of 10 moles per liter, the immersion bringing about the formation on the titanium of a layer of hydrated titanium oxides ($HTiO_{3-}$) which itself brings about the appearance of hydroxyl groups TiOH which allow the calcium phosphate film to be deposited, characterised in that it comprises, after the immersion operation of the implant in the sodium hydroxide, an anodisation operation of the implant under a given voltage which allows a stabilisation of the layer of oxides formed by the immersion operation in sodium hydroxide.

The voltage of the anodisation operation is advantageously in the order of from 50 to 110 volts.

Preferably, the voltage of the anodisation operation is a low voltage, and it is more preferably in the order of from 50 to 75 volts.

In a particularly advantageous operating method, the voltage of the anodisation operation is in the order of 50 volts.

According to a variant, the voltage of the anodisation operation is in the order of 110 volts.

According to another advantageous feature, each of the operations of immersion in the sodium hydroxide and anodisation of the method is followed by a rinsing operation.

The whole of the two operations of immersion in sodium hydroxide and anodisation may advantageously be followed by a drying operation, and in such a case the drying operation is carried out at a temperature in the order of 100° C.

According to a final feature, the whole of the operations indicated is followed by a standard cleaning/washing operation.

Of course, the present invention secondly relates to any titanium implant which is obtained by the implementation of a method which complies with the above-mentioned features.

The detailed specifications of the invention are given in the following description with reference to the appended drawings. It should be noted that these drawings are intended only to illustrate the text of the description and they therefore in no way constitute a limitation of the scope of the invention.

DESCRIPTION OF THE PREFERRED EMBODIMENTS OF THE INVENTION

Figure 1:
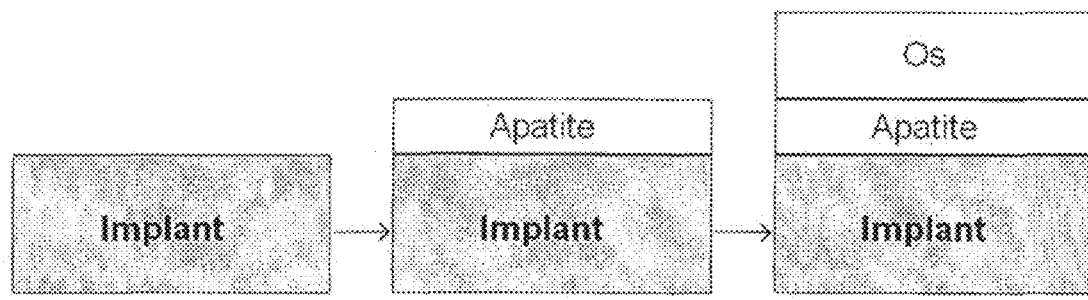
FIG. 1 is a flow chart of the process for attaching the bone to the implants irrigated by the bodily fluids, FIG. 2 reproduces the observations using a scanning electron microscope of a deposit of calcium phosphate on samples of pure titanium after 14 (on the left) and 28 (on the right) days of immersion in SBF.
Figure 2:
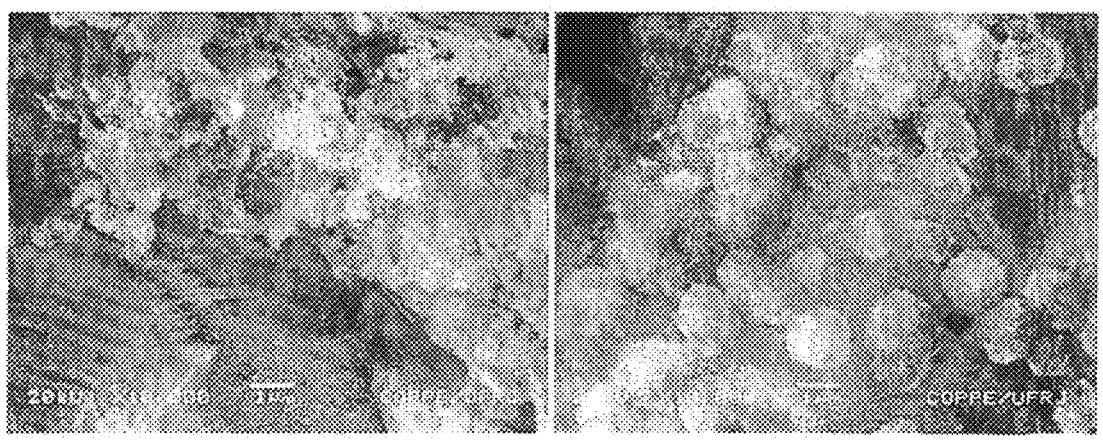

Prior to the detailed description of its invention, the filing company deems it necessary to point out that, in fields which are similar to that to which the invention directly relates, it is known to use techniques whose implementation comprises operations, some of which have some similarities to some of the operations carried out during the method according to the invention. However, these similar techniques could affect neither the novelty nor the originality of the present invention and further could not make it obvious, the objectives addressed by these different techniques being far removed and the operations carried out both before and after those which have some mutual similarities also being far removed from each other.

This is thus the case in particular for the method described in the international patent application to which the publication WO2009/044203 relates which involves carrying out an anodisation of metals in order to then integrate biocidal elements therein. The biocidal material used constantly in the context of this study is silver.

This method successively comprises the steps of cleaning by means of ultrasound a metal implant (for example, of titanium) which is immersed in a bath of acetone, followed by rinsing with deionised water, then cleaning in an alkaline solution of sodium hydroxide NaOH at 1M, then further rinsing with deionised water and finally anodisation between 50 V and 150 V in a solution of phosphoric acid whose concentration is preferably between 1 and 3 M.

The anodisation is then continued by using a voltage which is made negative, this voltage being in the order of from −0.2 V to −0.7 V, and the final processing phases involving, after these two anodisation operations, a third rinsing operation with deionised water followed by immersion in a solution containing a biocidal material, in this instance silver, as set out in the preamble.

Though this known method and the method of the present invention have in common operations of cleaning/pickling, rinsing, immersion in a solution of sodium hydroxide and anodisation, in order to improve the surface characteristics of some metal implants, and in particular titanium implants, these are all the aspects which they have in common.

In this manner, the common immersion phase in an alkaline solution of sodium hydroxide is a phase for cleaning the surface of the implant in the method of the prior art, carried out with a solution of concentrated 1M NaOH whilst, in the method according to the invention, the immersion in the solution of sodium hydroxide has to result in a modification of the chemical composition of the surface of the implant and it is therefore carried out with a solution of concentrated 10 M NaOH.

In this manner also, the anodisation phase of the method of the prior art is intended, as a result of the specific feature thereof which involves reversing the voltage, to ensure a processing of the surface of the implant, by creating porosities, whilst, in the method in accordance with the invention, the anodisation phase is intended to mechanically and chemically stabilise the layer of oxides formed at the surface of the implant, following immersion of the implant in the solution of concentrated 10 M sodium hydroxide. As a reminder, this layer of oxides does not exist in the method of the prior art since the immersion phase of the implant in the sodium hydroxide allows only simple cleaning of the surface of the implant since the concentration of 1 M is too weak to modify the composition of the surface.

In this manner, finally, as for the objectives, the method of the prior art is intended to create at the surface of the implant porosities at the centre of which there is placed a biocidal material whilst the method according to the invention is intended to improve the bioactivity of the implants by modifying the layer of oxides present on the surface and creating strong chemical bonds between this layer and the living medium, which can thus colonise it more rapidly and more solidly.

Figure 3:
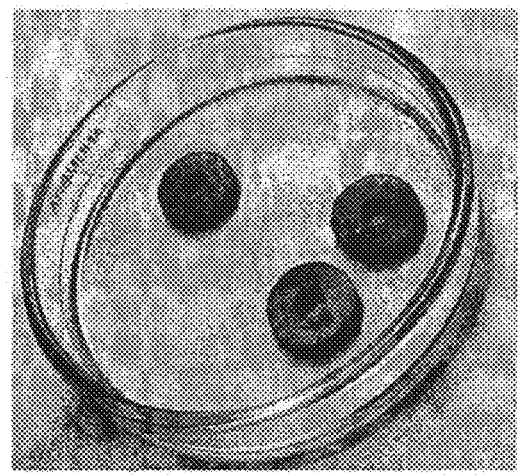
FIG. 3 shows an embodiment of samples, in the form of a perforated pellet, used for the bioactivity tests.
Figure 4:
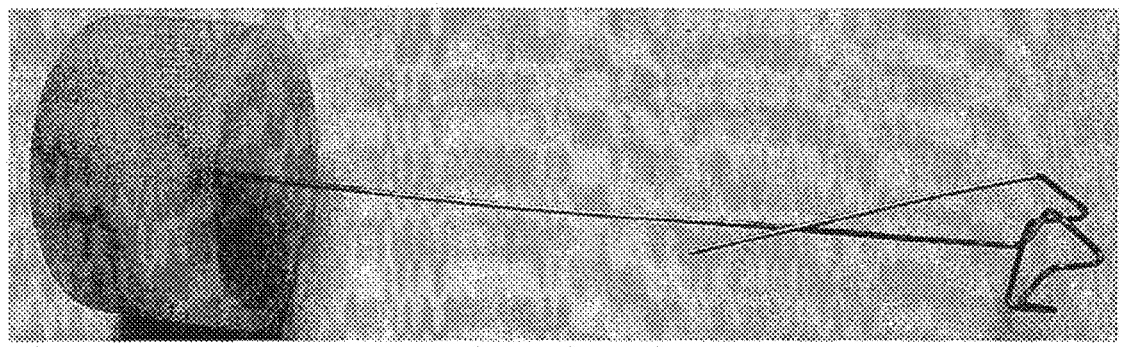
FIG. 4 shows a sample carrier which is intended to carry the pellets of FIG. 3, the sample carrier itself being fixed to the stopper of a bottle used for bioactivity tests.
Figure 5:
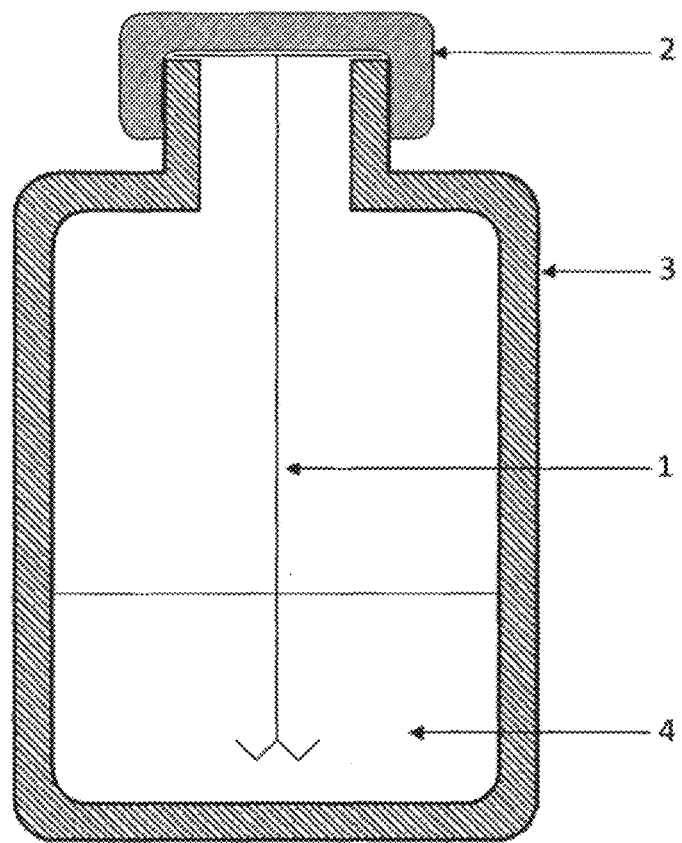
FIG. 5 is a vertical cross-section of the diagram of a bottle used for the above purposes, the bottle consequently containing the sample carrier and SBF.

These differences having been set out, in accordance with the invention a specific device has been developed, such a device allowing immersion tests to be carried out in SBF for samples which have been previously subjected to different surface treatments. This device and the different accessories thereof are illustrated in FIGS. 3 to 6. All the experiments carried out of course have in common the fact that they ultimately involve the immersion of samples of titanium in SBF for a defined period of time. Specific samples in the form of small pellets have been configured as shown in FIG. 3. These pellets, which are produced from grade 2 titanium, have a diameter of 10 mm and a thickness of 1.5 mm. The hole which is formed in the centre of these titanium pellets allows three of these pellets to be suspended on a sample carrier 1 which is produced from a wire of stainless steel which can be seen in FIG. 4. The wire is fixed at the centre of the stopper 2 of a bottle 3 containing SBF 4, which allows the samples to be immersed in the SBF in groups of three. FIG. 5 illustrates this principle.

Figure 6:
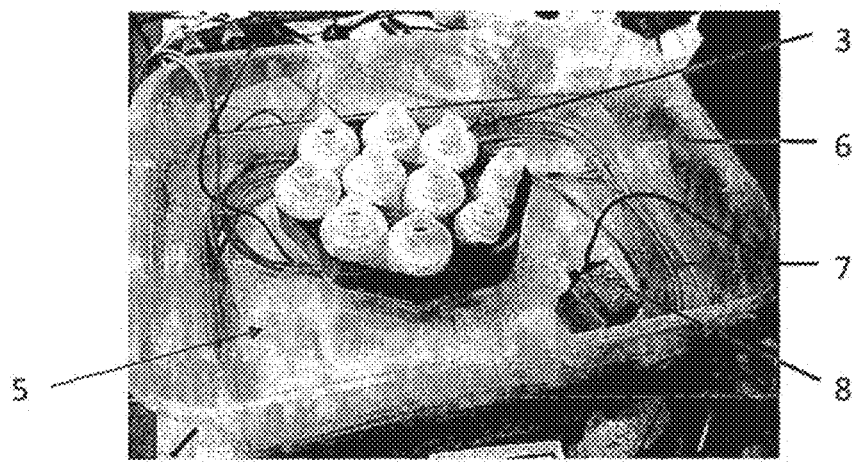
FIG. 6 is a view of the experimental device used, FIG. 7 sets out the modifications, according to Lenka, Jonasova and his team, of the surface of the titanium: during the pickling in HCl (a-b), during the processing with NaOH (b-c) and during the phases of depositing apatite in the SBF (d-f)
Figure 7:
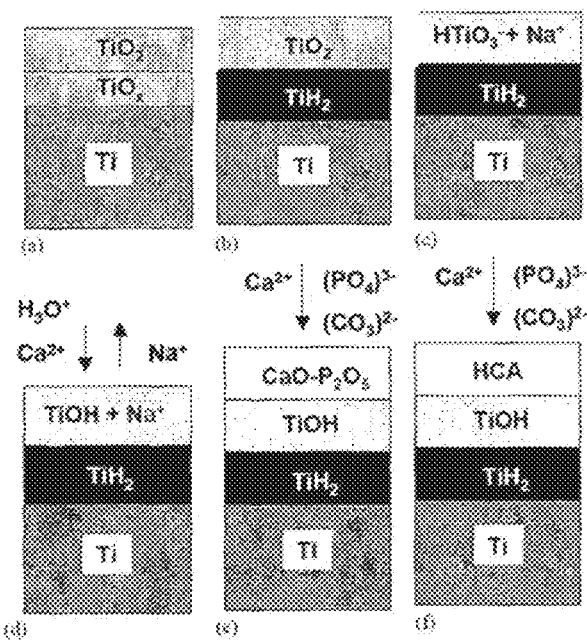

In order to represent the phenomena which take place within the human body, the final experiments of immersion mentioned above are carried out at a temperature of 37° C. To this end, the bottles 3 are immersed in a water bath 5 whose temperature is controlled at 37° C. FIG. 6 is a photograph of the experimental device. Bottles 3 which each contain three samples of titanium which have previously been subjected to the same surface treatment and which are bathed in SBF 4 are suspended on the cover (not illustrated) of the main vessel 6, and are moved by an agitation pump 8. The pump 8 simultaneously allows the temperature of the water which acts as a water bath to be homogenised, and allows the bottles which contain the samples of titanium and SBF to be agitated.

The method according to the present invention proposes joining an anodisation operation to the immersion operation in sodium hydroxide described in a patent application which is filed in parallel therewith, in order to overcome any chemical and mechanical instability of the effects of the processing with sodium hydroxide. In this regard, the Applicant filing the present patent application suspects that the implementation of an anodisation operation after the processing with sodium hydroxide described above could allow the oxides present on the surface of the titanium to be stabilised.

In order to evaluate and optimise this other processing operation, a programme of preliminary experiments for surface treatments and anodisations has been established. Table 3 sets out the five types of samples which have been produced in order to determine the influence of the surface treatment on the bioactivity thereof. The following processing operations have been carried out:

processing with 10 M sodium hydroxide coupled with anodisation carried out before or after the processing, in order to attempt to stabilise over time, chemically and mechanically, the layer of oxide produced by the processing with sodium hydroxide, anodisation at different voltages, before or after the processing with sodium hydroxide.

Each type of sample is produced in triplicate in order to ensure the repeatability of the operations carried out, defined in the following Table 3.

For all these surface treatment operations carried out by means of immersion in a solution of sodium hydroxide, a pickling operation was carried out beforehand using a solution containing fluoronitric acid $HFNO_3$. However, such a pickling operation could also have been carried out using a solution of hydrochloric acid.

TABLE 3

Different processing operations applied to the titanium samples

| A | B | C |
|---|---|---|
| Pickling HFNO3, 1 min | Pickling HFNO3, 1 min | Pickling HFNO3, 1 min |
| Rinsing operations | Rinsing operations | Rinsing operations |
| NaOH 10M, 60°., 24 h | NaOH 10M, 60°., 24 h | NaOH 10M, 60°., 24 h |
| Rinsing | Rinsing | Rinsing |
| Anodisation 50 V | Anodisation 75 V | Anodisation 110 V |
| Rinsing + Drying 100° C. | Rinsing + Drying 100° C. | Rinsing + Drying 100° C. |
| Standard cleaning/washing | Standard cleaning/washing | Standard cleaning/washing |

| D | E | F |
|---|---|---|
| Pickling HFNO3, 1 min | Pickling HFNO3, 1 min | Pickling HFNO3, 1 min |
| Rinsing operations | Rinsing operations | Rinsing operations |
| Anodisation 90 V | Anodisation 15 V | |
| Rinsing operations | Rinsing operations | |
| NaOH 10M, 60°., 24 h | NaOH 10M, 60°., 24 h | NaOH 10M, 60°., 24 h |
| Rinsing + Drying 100° C. | Rinsing + Drying 100° C. | Rinsing + Drying 100° C. |
| Standard cleaning/washing | Standard cleaning/washing | Standard cleaning/washing |

Analysis of the Results

After having received such surface treatments and anodisations, the different samples treated in this manner are immersed for one week in the SBF (r-SBF, see Table 2), then are observed by means of electronic microscopy. Chemical analyses are carried out in order to determine the composition of the apatite formed at the surface. Three chemical analyses on zones of 240×240 µm$^2$ are carried out on each sample in order to improve the statistics. It should be noted that the main components of the apatite are calcium and phosphorus. Their respective quantity defines the "quality" of the deposit formed. This is because a Ca/P ratio of between 0.5 and 2 is necessary in order to ensure that the deposit really is apatite (Driessens F. C. M., Boltong M. G., de Maeyer E. A. P., Wenz R., Nies B., Planell J. A., The Ca/P range of nanoapatitic calcium phosphate cements, Biomaterials 23, pages 4011-4017, 2002). Finally, it is also known that the greater the quantities of calcium and phosphorus are, the more efficient the processing operation is.

Figure 8:
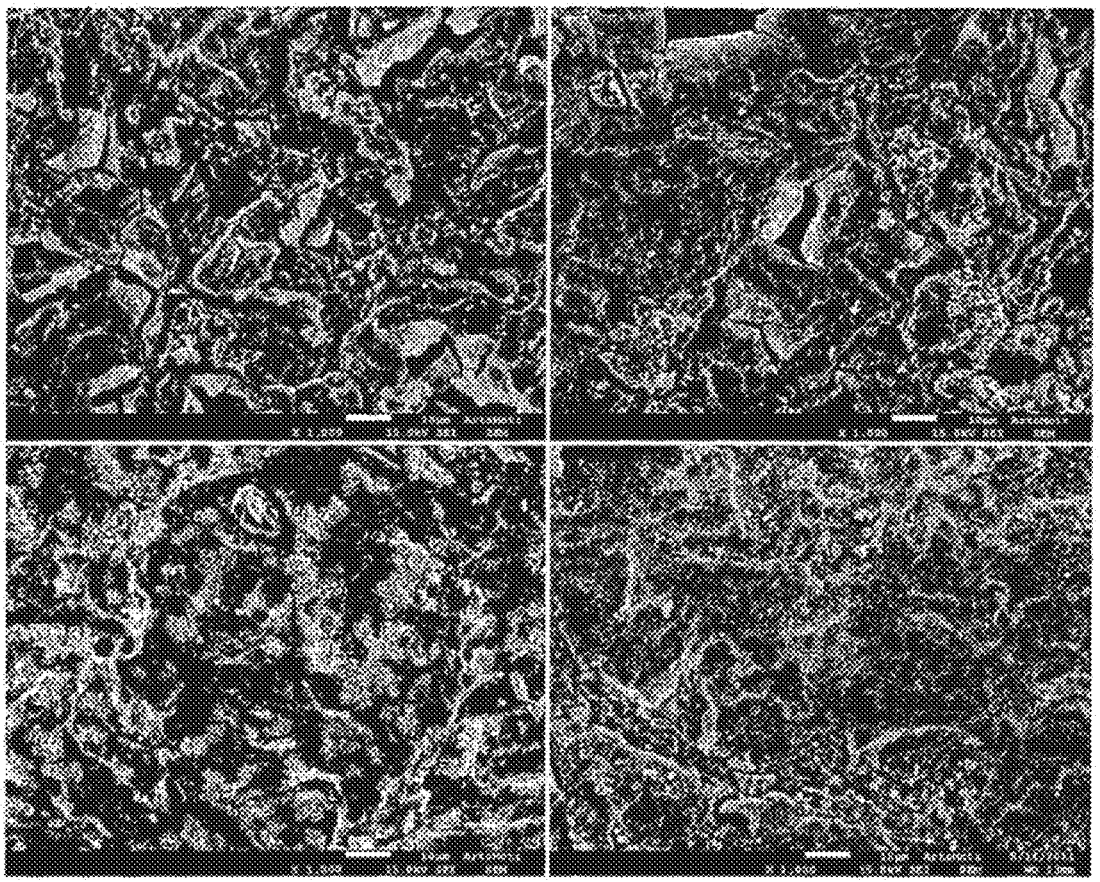
FIG. 8 is a comparison of the zones observed using scanning electron microscopy of the samples A, B, C and F, respectively, from left to right and then from top to bottom, after their immersion in the SBF.
Figure 9:
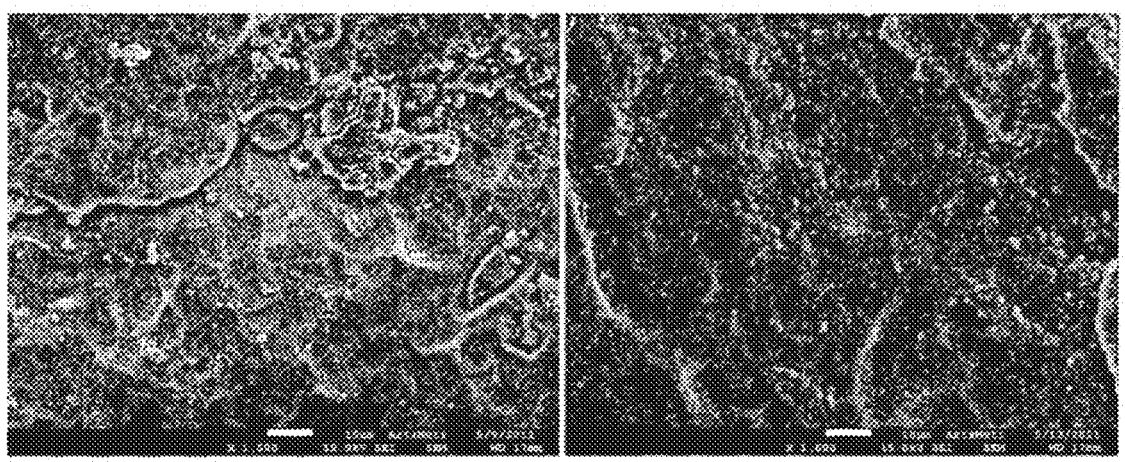
FIG. 9 is a comparison of the zones observed using scanning electron microscopy of the samples D (on the left) and E (on the right) after their immersion in SBF.

When comparing the data of Table 4 for the samples A, B and C, it should be noted that the anodisation voltage has an influence on the deposit which is carried out during the immersion. This is because a low voltage allows a significant deposit of calcium and phosphorus. The increase of the voltage causes the levels of these elements and the Ca/P ratio to fall. The NaOH+ anodisation processing is advantageous since, if the processing operations (A, B, C) are compared with a processing operation using only sodium hydroxide (sample F), it may be noted that the Ca/P ratio is far lower (less than 2 for NaOH+ anodisation against 4.3 for the NaOH processing only) as indicated in Table 4. The compound formed at the surface of the samples having been subjected to the two consecutive processing operations is therefore really apatite. Furthermore, it should be noted that the levels of calcium and phosphorus are much higher for the combined processing operations at a low anodisation voltage than for the processing operation with sodium hydroxide alone. With reference to FIG. 8, it can be seen that the anodisation voltage has a large influence on the surface state of the samples. At a low voltage, the layer originating from the sodium hydroxide processing is altered but the scales which are characteristic of a surface processed with sodium hydroxide can be seen, as the image of sample F shows. At a medium voltage, the scales are larger but still present. Conversely, for a voltage of 110 V, the layer which is processed with sodium hydroxide appears to have been totally modified; an oxidised surface can be seen in FIG. 8. This leads to a Ca/P ratio of 1.22, a ratio which is advantageous, but the quantities of calcium and phosphorus are nonetheless lower than for the samples A and B.

The samples D and E have been subjected to a combined reverse treatment: anodisation, then NaOH. It has appeared to be desirable to determine the influence of the preparation of the surface of the samples with a controlled anodisation before carrying out the processing with 10 M sodium hydroxide. In contrast to the samples A, B and C, the anodisation has therefore taken place before the processing with NaOH. After immersion, an anodisation at low voltage (sample E) allows the levels of calcium and phosphorus to be increased whilst causing the Ca/P ratio to fall relative to the processing with NaOH alone. The anodisation at high voltage (sample D) brings about a deposit of phosphorus which is equivalent to processing with NaOH alone, but a less significant deposit of calcium. This brings about a much lower Ca/P ratio.

The processing by means of anodisation followed by immersion in NaOH is therefore less efficient than the NaOH processing followed by an anodisation. This is because it brings about a deposit of calcium and phosphorus of much lower quantity and a higher Ca/P ratio. The processing with sodium hydroxide has the effect of destroying the layer of $TiO_2$ in order to replace it with an oxide of hydrated titanium. The anodisation carried out before the processing with sodium hydroxide causes the thickness of the layer of $TiO_2$ initially present on the surface of the titanium to increase. This makes the process of deoxidisation by means of sodium hydroxide much more difficult. In this manner, the effect of processing with sodium hydroxide is reduced.

When comparing these results with the analyses carried out on the sample F, according to Table 4, it can be seen that the deposit on this sample has the highest Ca/P ratio. The deposit is therefore of lower quality than those present on the other samples. Furthermore, it should be noted that the levels of calcium and phosphorus on the sample F are not very high. This is because the samples A and B have a quantity of calcium and phosphorus which is much higher for an advantageous Ca/P ratio.

TABLE 4

Mean of the level of Ca and P present at the surface of the samples and corresponding Ca/P ratio after their immersion in the SBF

|   | Ca | P | Ca/P |
|---|---|---|---|
| A | 1.45 ± 0.03 | 0.86 ± 0.05 | 1.68 ± 0.06 |
| B | 1.21 ± 0.05 | 0.58 ± 0.04 | 2.07 ± 0.08 |
| C | 0.47 ± 0.09 | 0.39 ± 0.07 | 1.22 ± 0.18 |
| D | 0.62 ± 0.11 | 0.23 ± 0.05 | 2.73 ± 0.23 |
| E | 1.22 ± 0.16 | 0.39 ± 0.07 | 3.10 ± 0.20 |
| F | 0.99 ± 0.05 | 0.23 ± 0.04 | 4.29 ± 0.59 |

SUMMARY

The invention proposes a new surface treatment based on processing with sodium hydroxide at a concentration in the order of 10 M followed by an anodisation. The anodisation has to stabilise the layer of oxides formed by the processing with sodium hydroxide. It has further been shown that the processing which involves immersion in sodium hydroxide then anodisation is much more efficient than a processing operation with sodium hydroxide alone as described in documentation.

The processing with sodium hydroxide proposed in the other patent application and coupled with an anodisation at 50 V is ideal. The result after immersion for one week in SBF is a Ca/P ratio which is similar to that of the human bone and consistent levels of calcium and phosphorus.

Text in FIG. 1: Os=Bone

The invention claimed is:

1. A method of surface treatment of a bioinert titanium implant configured to be placed in contact with a bone of a human body, wherein a flow of biological fluids such as a mineral part of human blood plasma is allowed, to deposit a calcium phosphate film on the titanium implant in order to make the bioinert titanium implant bioactive, so as to allow a chemical bond between the bone and the implant, thus favoring an osseointegration, the method comprising a step of immersing the titanium in a solution comprising sodium hydroxide, the immersion resulting in a formation on the titanium of a layer of hydrated titanium oxides, which results in the appearance of hydroxyl groups, allowing for the depositing of the calcium phosphate film, wherein the method further comprises, after the immersion of the implant in the sodium hydroxide, another step of anodizing the implant at a given voltage to stabilize the oxide layer formed by the immersion in the sodium hydroxide.

2. The method of claim 1, wherein the voltage of the step of anodizing is in the order of from 50 to 110 volts.

3. The method of claim 2, wherein the voltage of the step of anodizing is in the order of from 50 to 75 volts.

4. The method of claim 2, wherein the voltage of the step of anodizing is in the order of 110 volts.

5. The method of claim 2, wherein the voltage of the step of anodizing is in the order of 50 volts.

6. The method of claim 1, further comprising a rinsing step after each of the steps of immersion in the sodium hydroxide and anodization.

7. The method of claim 1, further comprising a drying operation.

8. The method of claim 7, wherein the drying operation happens after the step of anodizing the implant.

9. The method of claim 7, wherein the drying operation is carried out at 100° C.

10. The method of claim 1, further comprising a standard cleaning and washing operation.

11. The method of claim 10, wherein the standard cleaning and washing operation happens after the step of anodizing the implant.

* * * * *